United States Patent
Testoni

(10) Patent No.: US 6,996,492 B1
(45) Date of Patent: Feb. 7, 2006

(54) SPECTRUM SIMULATION FOR SEMICONDUCTOR FEATURE INSPECTION

(75) Inventor: Anne L. Testoni, Bolton, MA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 36 days.

(21) Appl. No.: 10/804,826

(22) Filed: Mar. 18, 2004

Related U.S. Application Data

(60) Provisional application No. 60/456,104, filed on Mar. 18, 2003.

(51) Int. Cl.
*G01K 11/30* (2006.01)

(52) U.S. Cl. ..................... 702/134; 378/137

(58) Field of Classification Search ............ 702/35, 702/36, 40, 75–77, 117, 118, 183, 185, 189, 702/134, 135; 378/45, 54, 56, 58, 62, 137; 703/18; 250/363.02, 310
See application file for complete search history.

(56) References Cited

U.S. PATENT DOCUMENTS

| | | | |
|---|---|---|---|
| 6,067,342 A * | 5/2000 | Gordon ..................... 378/19 |
| 6,201,850 B1 * | 3/2001 | Heumann ................... 378/56 |
| 6,407,386 B1 | 6/2002 | Dotan et al. ................ 250/310 |
| 6,409,383 B1 * | 6/2002 | Wang et al. ................ 378/207 |
| 6,459,761 B1 * | 10/2002 | Grodzins et al. ............ 378/57 |
| 6,567,496 B1 * | 5/2003 | Sychev ...................... 378/57 |
| 6,754,298 B2 * | 6/2004 | Fessler ....................... 378/4 |
| 6,817,735 B2 * | 11/2004 | Shimizu et al. ............ 362/231 |
| 2001/0018891 A1 * | 9/2001 | Loesch et al. ............. 117/200 |
| 2002/0149305 A1 * | 10/2002 | Danielsson et al. ... 313/105 CM |

\* cited by examiner

*Primary Examiner*—Marc S. Hoff
*Assistant Examiner*—Mohamed Charioui
(74) *Attorney, Agent, or Firm*—Beyer Weaver & Thomas LLP

(57) ABSTRACT

Techniques for determining certain parameters of semiconductor specimens using X-ray spectroscopy are described. The invention can be used to determine parameters such as composition, dimensions, and density of semiconductor specimens. Specifically, an X-ray spectrum simulation algorithm is used to iteratively generate a theoretical X-ray spectrum for a semiconductor specimen having certain parameters. The iterative generation of theoretical X-ray spectrums continues until one of the theoretical X-ray spectrum closely matches the actual X-ray spectrum measured off of the specimen. In an alternative embodiment, this technique of generating theoretical X-ray spectrums can be used in combination with a pre-existing library of X-ray spectral signatures for semiconductor specimens having various parameters.

19 Claims, 4 Drawing Sheets

SPECTRUM SIMULATION FOR SEMICONDUCTOR FEATURE INSPECTION

CROSS-REFERENCE TO RELATED APPLICATIONS

This application claims priority of U.S. provisional patent application No. 60/456,104, filed Mar. 18, 2003, entitled "Spectrum Simulation for Semiconductor Feature Inspection," which is hereby incorporated by reference.

FIELD OF THE INVENTION

The present invention relates generally to semiconductor inspection techniques, and more specifically to such techniques that utilize x-ray spectroscopy.

BACKGROUND OF THE INVENTION

Generally, the semiconductor manufacturing industry involves highly complex techniques for integrating circuits into semiconductor materials. Due to the large scale of circuit integration and the decreasing size of semiconductor devices, the semiconductor manufacturing process is prone to processing defects. Semiconductor defects may include structural flaws, residual process material and other surface contamination, which occur during the production of semiconductor wafers. Defects can be introduced to a wafer at any process step in wafer production. For example, a particle defect may originate from contamination during a deposition process or it may be introduced to the wafer due to exposure during a wafer transfer from one process chamber to another. As another example, a scratch defect may occur due to abrasive polishing during a chemical mechanical planarization process, or it may occur due to faulty cleaning process or it may occur from operator error during wafer handing. Since defects can have a similar appearance but originate from different process steps, it can be difficult to find root causes of the defects, such as a faulty process.

To help detect and locate defects, a class of instruments called inspection tools is used. Inspection tools inspect the wafers at various critical points between process steps in wafer production. Such instruments scan wafer surfaces using a variety of techniques and detect and record the location of anomalies. Typically, these techniques involve directing a light or electron beam towards the surface of the semiconductor where the defect is, and detecting the resultant light reflected off or electrons emitted from the sample. The reflected light or emitted electrons may then be used to generate a target image of the surface of the semiconductor. In some typical inspection processes, differences between the target image and a reference image (which is known to contain no defects) are determined and, when the differences are above a predetermined threshold, it may be determined that a defect exists. In other typical inspection processes, similar semiconductor device areas are compared against each other and the detected feature differences between device areas are identified as potential defects.

To obtain specific information about a located defect or any other feature on a semiconductor substrate, additional techniques are typically employed. Examples of such specific information include the composition, size, and density of each defect. One category of techniques used to measure such information is x-ray spectroscopy, which includes X-ray fluorescence testing and X-ray micrography. Unfortunately, X-ray spectroscopy has certain inherent characteristics that effect the accuracy of measurements. For example, the high energy electron beam required to cause X-rays to emanate from a semiconductor sample cause X-rays to emanate from regions that extend beyond the specific defect being reviewed. The resulting data therefore does not reflect accurately upon the defect since data relating to areas surrounding the defect is also included. Since testing procedures are an integral and significant part of the manufacturing process, a more accurate X-ray review process would be desirable.

BRIEF SUMMARY OF THE INVENTION

The present invention pertains to an application of X-ray spectroscopy to determine certain parameters of semiconductor specimens. Specifically, an X-ray spectrum simulation algorithm is used to iteratively generate a theoretical X-ray spectrum for a semiconductor specimen having certain parameters. The iterative generation of theoretical X-ray spectrums continues until one of the theoretical X-ray spectrum closely matches the actual X-ray spectrum measured off of the specimen. In an alternative embodiment, this technique of generating theoretical X-ray spectrums can be used in combination with a pre-existing library of X-ray spectral signatures for semiconductor specimens having various parameters.

As a method and a computer readable medium, one embodiment of the present invention includes at least, scanning a region of interest with an electron beam to cause X-rays to emanate from the region of interest;

detecting the X-rays from the region of interest using at least one X-ray detector wherein the detected X-rays are within a certain energy range spectrum and thereby form an experimental X-ray spectrum;

selecting a reference spectrum from an X-ray spectrum library based upon a set of inspection system parameters, a set of known semiconductor specimen parameters, and an initial estimated value for the unknown parameter;

generating a simulated spectrum using a spectrum simulation algorithm based upon the set of inspection system parameters, the set of known semiconductor specimen parameters, and the initial estimated value for the unknown parameter, wherein the simulated spectrum is generated when an appropriate reference spectrum is not part of the X-ray spectrum library;

comparing the experimental X-ray spectrum against either the reference spectrum or the simulated spectrum and determining the degree to which the experimental X-ray spectrum matches either the reference or simulated spectrum;

when the experimental X-ray spectrum does not match the reference or simulated spectrum to a satisfactory degree, repeating the selecting, generating, and comparing operations wherein a new estimated value for the unknown parameter is used in place of the initial estimated value for the unknown parameter; and when the experimental X-ray spectrum does match the reference or simulated spectrum to a satisfactory degree, determining that the estimated value for the unknown parameter used to select the reference spectrum or to generate the simulated spectrum is approximately equal to the actual value of the unknown parameter.

In another method implementation, the invention primarily obtains reference spectrums by generating X-ray spectrums with a simulated spectrum algorithm.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

The present invention pertains to an application of X-ray spectroscopy to determine certain parameters of semiconductor specimens. For example, the invention can be used to determine parameters such as composition, dimensions, and density of semiconductor specimens. Specifically, an X-ray spectrum simulation algorithm is used to iteratively generate a theoretical X-ray spectrum for a semiconductor specimen having certain parameters. The iterative generation of theoretical X-ray spectrums continues until one of the theoretical X-ray spectrum closely matches the actual X-ray spectrum measured off of the specimen. This technique of generating theoretical X-ray spectrums can optionally be used in combination with a pre-existing library of X-ray spectral signatures for semiconductor specimens having various parameters. In this configuration, the analysis process primarily compares an experimentally measured X-ray spectrum against X-ray spectrums stored in the library, and uses the spectrum simulation algorithm as backup when an X-ray spectrum for a semiconductor specimen having certain parameters is not present in the library.

Figure 1:
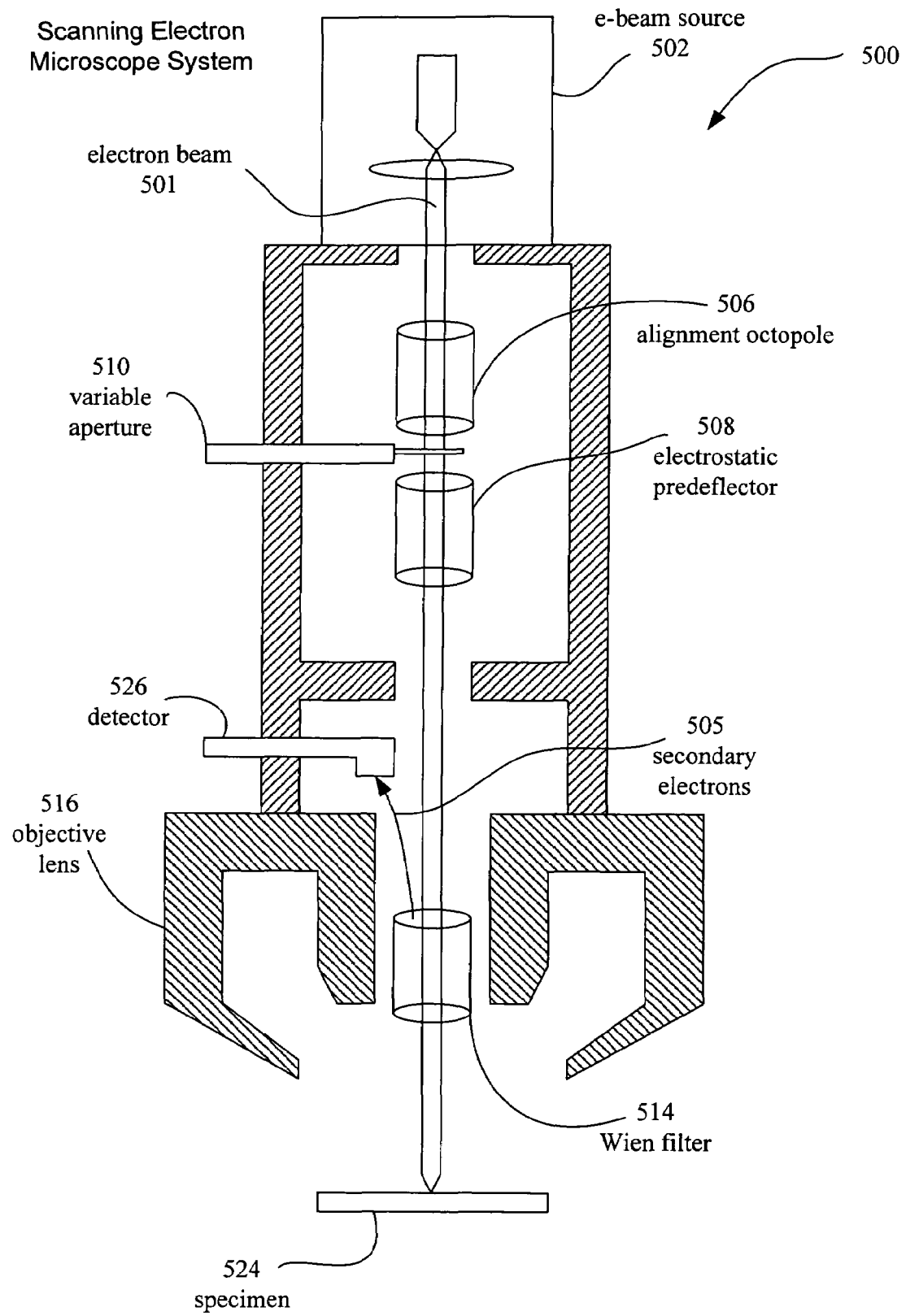
FIG. 1 illustrates a diagrammatic view of one embodiment of a scanning electron microscope that can be used to implement the present invention.

FIG. 1 illustrates a diagrammatic view of one embodiment of a scanning electron microscope (SEM) 500 that can be used to implement the present invention. As shown, SEM system 500 includes an electron beam generator (502 through 516) that generates and directs an electron beam 501 substantially toward a region of interest on a specimen 524. The SEM system 500 may also include a detector 526 arranged to detect charged particles 205, such as secondary electrons, backscattered electrons, and X-rays, emitted from sample 524. The SEM may also include an image generator (not shown) for forming an image from the emitted particles.

The electron beam generator may be arranged in any suitable configuration for generating an electron beam that will cause secondary and backscatter electrons and/or X-rays to emanate from sample 524. In one embodiment, the electron beam generator can include an electron source unit 502, an alignment octupole 506, an electrostatic predeflector 508, a variable aperture 510, a wien filter 514, and a magnetic objective lens 516. Source unit 502 may be implemented in any suitable form for generating and emitting electrons. For example, source unit 502 may be in the form of a filament that is heated such that electrons within the filament are excited and emitted from the filament. Octupole 506 is configured to align the beam after a particular gun lens voltage is selected. In other words, the beam may have to be moved such that it is realigned with respect to aperture 510.

Aperture 510 forms a hole through which the beam is directed. The lower quadrupole 508 may be included to compensate for mechanical alignment discrepancies. That is, lower quadrupole 508 is used to adjust the alignment of the beam with respect to any misaligned through-holes of the SEM through which the beam must travel.

Wien filter 514 provides a B×E field (e.g., a magnetic field's direction is perpendicular and directed away from a direction of an electric field) that is normal to the electron beam is path. Wien filter 514 applies an E force on the beam that is opposite to the B force that is applied on the beam. Thus, Wien filter does not substantially move the beam off axis. However, Wien filter 514 applies the E force and B force on secondary electrons emitted from the sample in a same direction that is towards the detector 526. Thus, Wien filter 514 deflects secondary electrons towards the detector 526. Wien filter 514 and/or octopole 506 and/or quadrupole 508 may be configured to direct the beam across an area of the sample. By setting the X and Y scan voltages, a particular beam pattern may be selected. The deflection system may include a processor that may be also configured to control voltage settings on the electrodes, as well as scan voltages, as a function of incident beam position.

Magnetic objective lens 516 provides a mechanism for fine focusing of the beam on the sample. A plurality of electrostatic lens (not shown) may provide fast focus of the beam onto the sample surface. SEM system 500 may include a support or stage (not shown) for supporting the sample 524.

SEM system 500 may include a detector 526 for generating a detected signal from the detected secondary and/or backscattered electrons, or alternatively X-rays emitted from the sample in response to the electron beam. The detector may take the form of a micro-channel plate, micro-sphere plate, semiconductor diode, a scintillator/photomultiplier (PMT) assembly, an Energy Dispersive System (EDS), or a wavelength dispersive system (WDS) detector.

SEM system 500 may also include an image generator (not shown) arranged to receive the detected signal and generate and/or store an image. The image generator is operable to generate an image based on the detected signal. Thus, SEM system 500 may also include an analog to digital converter for converting the detected signal into a digital signal. SEM system 500 may also include a computer system for processing the image frame data to generate an image of the sample. For example, successive image frame data may be averaged together to create the image.

Typically, sample 524 and the electron beam are enclosed within a vacuum environment. The vacuum chamber should be large enough to enclose a semiconductor wafer. SEM system 500 is configured to inspect very small features and defects on samples such as semiconductor wafers.

Figure 2:
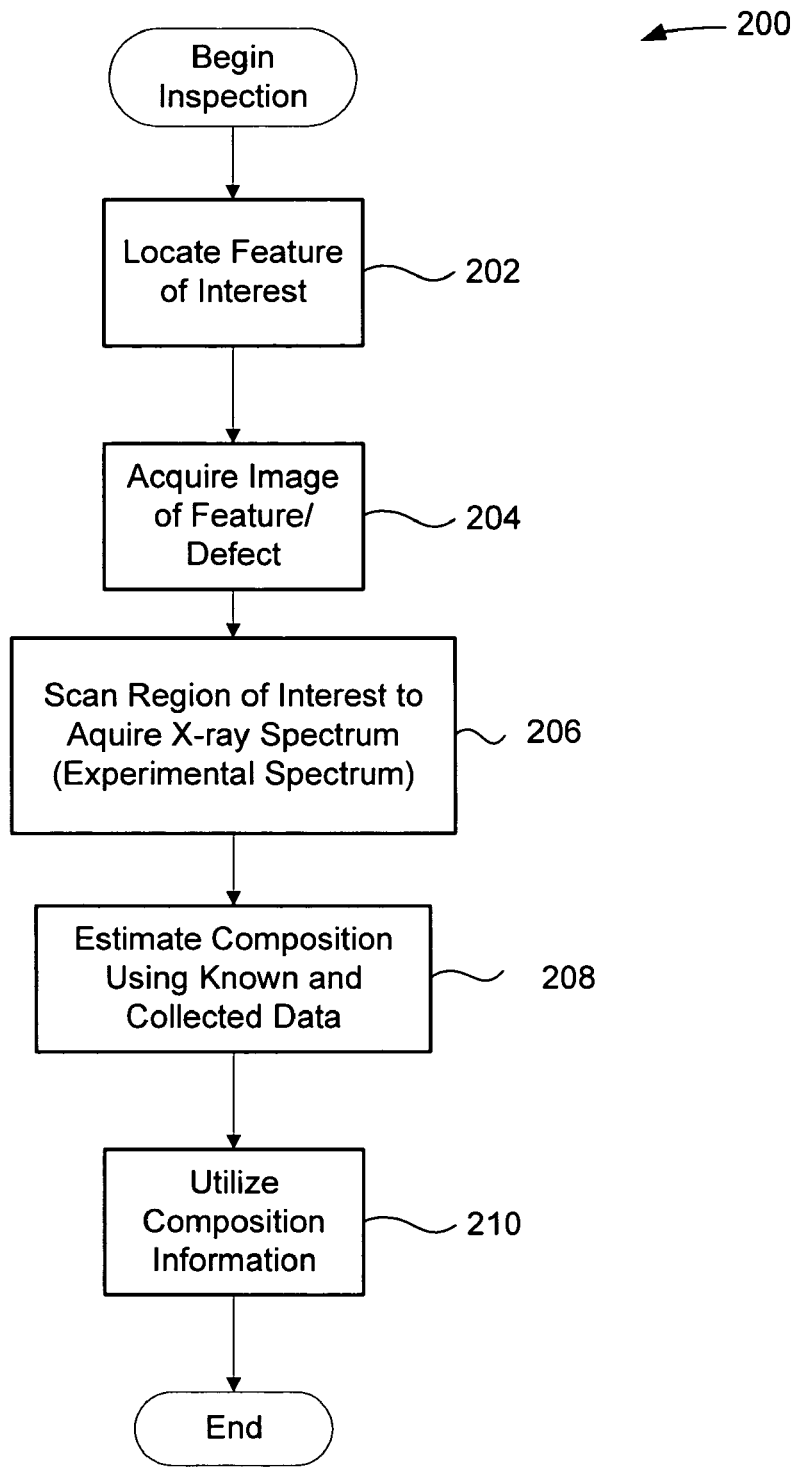
FIG. 2 illustrates a flow diagram that represents the basic operations involved with an analysis technique according to one embodiment of the present invention.

FIG. 2 illustrates a flow diagram that represents the basic operations involved with an analysis technique 200 according to one embodiment of the present invention. The process described in technique 200 is described as being implemented with a charged particle beam system, such as a scanning electron microscope as shown in FIG. 1. The process is also described as it would be used to determine the composition of a semiconductor specimen, even though it can easily be modified to determine other parameters such as size dimensions and density values. Density can refer to the amount of voids in the feature per unit volume, while size can refer to the thickness or dimensions of the feature.

The composition analysis technique 200 begins at block 202 where an area of interest is located on a specimen to be inspected. The area of interest can be a defect or a specific feature that requires analysis. For instance, a feature that may need analysis could be a via or an integrated circuit component, and a defect could be a scratch or a contaminated region. An area of interested can be located by using a library containing the location of various pre-determined areas of interest. For example, such a library can contain the design layout of a semiconductor wafer. This library can also be populated by obtaining information through an inspection process, such as an optical or charged particle inspection process. After a defect or area of interest is located, the field of view of the charged particle beam system is moved over the feature or area.

In block 204, an image of the defect, feature, or area of interest is acquired. This image can be acquired with various devices such as a charged particle beam system or an optical system. The charged particle beam system can form the image using secondary electron and/or backscatter electron detectors. After an image of the area of interest is generated, information about the area of interest is collected. For instance, dimensions of the features or defects within the area of interest can be collected. These dimensions include length, width, largest dimension, area and overall shape types such as rectangular, circular, needle-like or irregular. The collected information from the image, along with other information regarding the inspection system and the semiconductor specimen, are used in later stages of the analysis.

In block 206, the region of interest is scanned with the electron beam of the SEM so that X-rays emanate from the semiconductor specimen and then can be collected. Typically, the area is scanned in a raster pattern. In order to scan the area of interest, the SEM is required to have certain settings adjusted. For instance, the incident beam current level of the SEM should be set to a level appropriate for the specimen. Also, the amount of time during which backscatter electrons will be measured should be set. This amount of time is referred to as the "acquisition time." The acquisition time will be selected based on the size of the feature of interest and the type, structure, and composition of the semiconductor wafer substrate.

X-ray detectors within the SEM system are arranged to detect and measure the X-ray emission levels at the various energy levels. The measured X-rays are typically represented on a two-dimensional graph wherein the x-coordinate represents an energy range (e.g., in KeV) and the y-coordinate represents the intensity of X-rays at each of the energy levels. Intensity can be measured in, for example, counts/second/KeV. For each region to be inspected, an X-ray spectrum is collected. The collected X-ray spectrum is referred to as an "experimental spectrum" (ES).

In block 208, the composition of the region of interest is determined using an iterative process wherein the experimental spectrum is compared to reference X-ray spectrums, which are representative of specimens having known parameters. When a satisfactory match between the experimental spectrum and a reference X-ray spectrum is found, the parameters of the reference spectrum are taken to be an accurate estimate for the actual specimen. When the details of block 208 are described in FIG. 3 below, it will be shown that simulated X-ray spectrums that are generated with a spectrum simulation algorithm can also be compared against the experimental spectrum.

In block 210, the parameters of the semiconductor specimen determined in block 208 can be used in further specimen inspection processes. For example, the information can be used to tune another inspection system to the type of material within the specimen. Specifically, the energy of a charged particle beam can be set to the lowest energy level appropriate for the specific material type so that accurate measurements can be obtained. Higher energy levels than necessary cause a charged particle beam to irradiate more than the desired area to be inspected, which causes inaccurate measurements. Additionally, this is a waste of energy. Also, when a defect is determined to be a low atomic number (Z<20) element, an electron optical column can be optimized for low atomic number elements. On the other hand, when a defect exhibits a high atomic number element signature, a high kilovolt electron beam is usually determined to be more suitable for further inspection.

The composition information also can be used to improve the accuracy of defect classification techniques. For example, the composition information can be used to sort features or defects into bins (or categories) according to composition or atomic numbers. One example of a set of bins has bins of the categories of: low atomic number, mid-atomic number, transition metal, and heavy elements. An alternative set of bins is categorized by atomic numbers wherein each bin includes defects having atomic numbers within a specific range. For example, each bin can cover a range of 5 atomic numbers.

Figure 3:
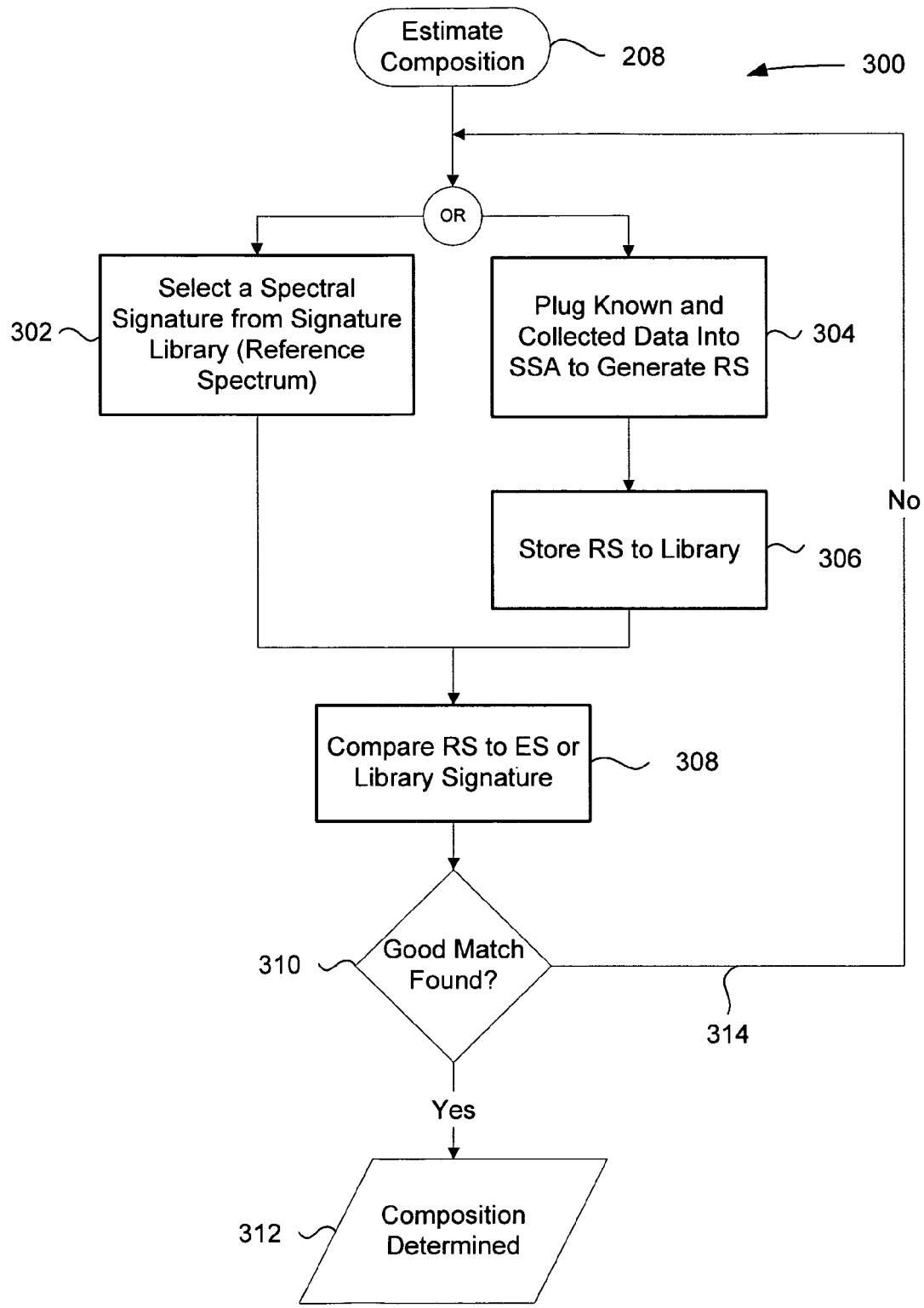
FIG. 3 illustrates a process flow for the sub-steps of block of FIG. 2 according to one embodiment of the present invention.

FIG. 3 illustrates a process flow 300 for the sub-steps of block 208 of FIG. 2 according to one embodiment of the present invention. Again, these sub-steps are used to determine the composition of the semiconductor specimen. Process flow 300 can proceed in a couple of manners to obtain a reference X-ray spectrum for comparison against the experimental spectrum measured in block 206 of FIG. 2. The first method of obtaining a reference X-ray spectrum shown in block 302 is to utilize a library of X-ray spectrums that have been predetermined and represent respective semiconductor specimens having specific parameters. Such specific parameters include the size, shape, and layout of the specimen. And the other method for obtaining a reference X-ray spectrum as shown in block 304 is to use a spectrum simulation algorithm (SSA). The SSA is an algorithm especially designed to generate an X-ray spectrum when provided certain input parameters that relate to the feature being analyzed.

The parameters needed to select the reference spectrum from the library (block 302) or to use as input variables into the SSA include specimen information, electron beam settings, X-ray detector information, and an initial estimate of the parameter sought to be measured by the inspection system. As mentioned above, the specimen information can include the size, shape, and layout of the inspected area of the semiconductor specimen. This information is typically information about an ideal configuration of the specimen, that is, one without defects. This information is in part obtained from the image acquired in block 204 of FIG. 2. The specimen information of the features can be approximate in value. The electron beam parameters include information relating to, for example, the incident beam energy, incident beam angle, raster size and dimensions, beam current, and the collection time. The X-ray detector information includes information such as the detector type, energy resolution, reference energy for energy resolution, solid angle of each detector, and polar and azimuthal angles. Finally, the last bit of information needed to either select or generate a reference X-ray spectrum is the initial estimate (or seed value) of the parameter that is being determined. For example, an initial approximation of the Atomic number of the inspected region is selected in order to select an X-ray spectrum from the library or to plug into the SSA. One method to select the initial estimate is to perform a quick analysis of the actual X-ray spectrum obtaining in block 206 of FIG. 2.

In one embodiment, the first option is to utilize reference X-ray spectrums from the library to compare against the experimentally obtained X-ray spectrum. However, given the vast number of variations in the semiconductor parameters, it is likely that the library will lack X-ray spectrums for some semiconductor specimen configurations. It is at this time, that the SSA of block 304 can be utilized to generate a simulated X-ray spectrum for the desired semiconductor specimen parameters.

Then in block 306, the simulated X-ray spectrum generated by the SSA can be optionally stored into the X-ray spectrum library for future reference. In this way, the X-ray spectrum library will have a larger number of X-ray spectrums to select from in future analyses.

An alternative embodiment of the invention uses only the SSA of block 304 to generate simulated X-ray spectrums. In other words, a new and simulated X-ray spectrum is generated at each iteration of the analysis without accessing any library of X-ray spectrums.

In another embodiment, it may be determined that the experimentally acquired spectrum is only to be compared against reference spectrums within the library.

In block 308, the reference X-ray spectrum obtained from the library or generated with the SSA is compared against the experimentally measured X-ray spectrum. In block 310, a decision is made as to whether the reference or simulated spectrum and the experimental spectrum match within a certain tolerance. For instance, comparison of the location of characteristic peaks and various slopes of within the spectrums are compared side-by-side. The degree to which the reference or simulated spectrum and the experimental X-ray spectrums match can be determined through mathematical comparison techniques, such as simplex methods. Exemplary simplex methods include the as chi-squared and least square means methods. Each of these techniques output a "goodness of fit value." When this value exceeds a certain threshold, a good fit is found. Various well-known techniques can be used for finding a "good fit."

When it is determined that a good match between the reference or simulated spectrum and the experimental X-ray spectrums has not been found, dynamic flow line 314 shows that control of the process returns to the beginning of process 300. Then, the sub-steps are repeated so that a new reference spectrum from the X-ray library or a new simulated X-ray spectrum generated by the SSA can be obtained and then compared against the experimental spectrum. A new reference or simulated spectrum is obtained by adjusting the value of the parameter that is sought to be determined. For example, when trying to determine the composition of the region of interest, a new atomic number is used to select or generate the new reference spectrum. Ideally, the newly selected atomic number and the resultant reference X-ray spectrum is a closer match to the actual atomic number and the experimental spectrum, respectively. Of course, the other parameters can also be adjusted at each iteration if required.

Eventually, when a good match is determined in decision block 310, the atomic number used to select the reference spectrum is deemed to be an accurate estimate of the atomic number of the material in the region of interest on the semiconductor specimen. The composition of the material is the output 312 of the iterative process described in process 300. Of course, if the inspection technique is used to determine another parameter of the specimen, then the reference X-ray spectrum provides an accurate estimate of the desired parameter.

Figure 4:
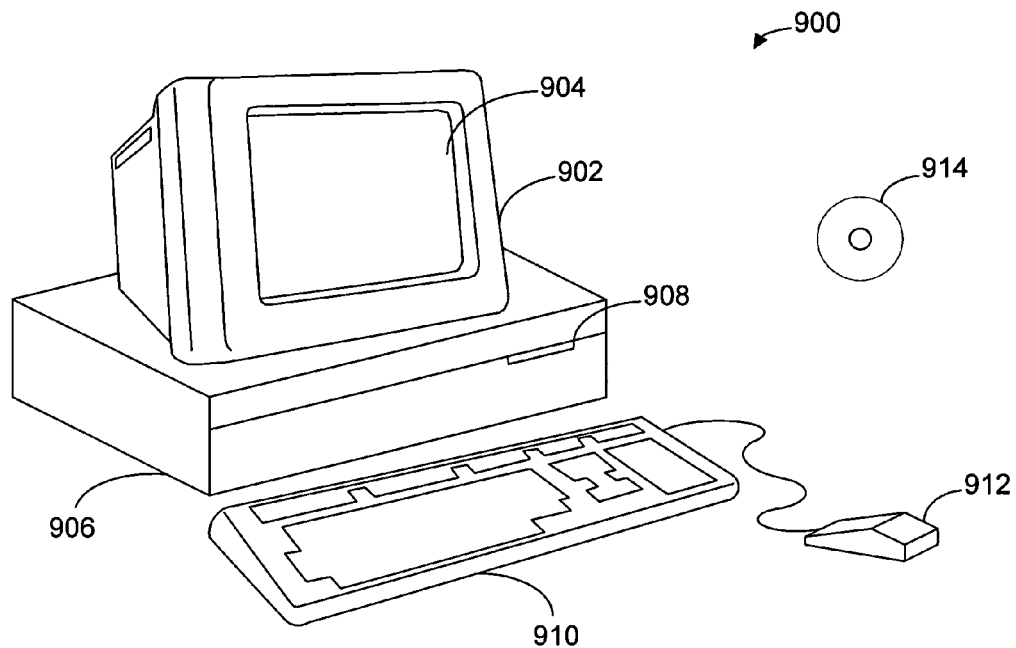
FIGS. 4 and 5 illustrate a computer system suitable for implementing embodiments of the present invention.
Figure 5:
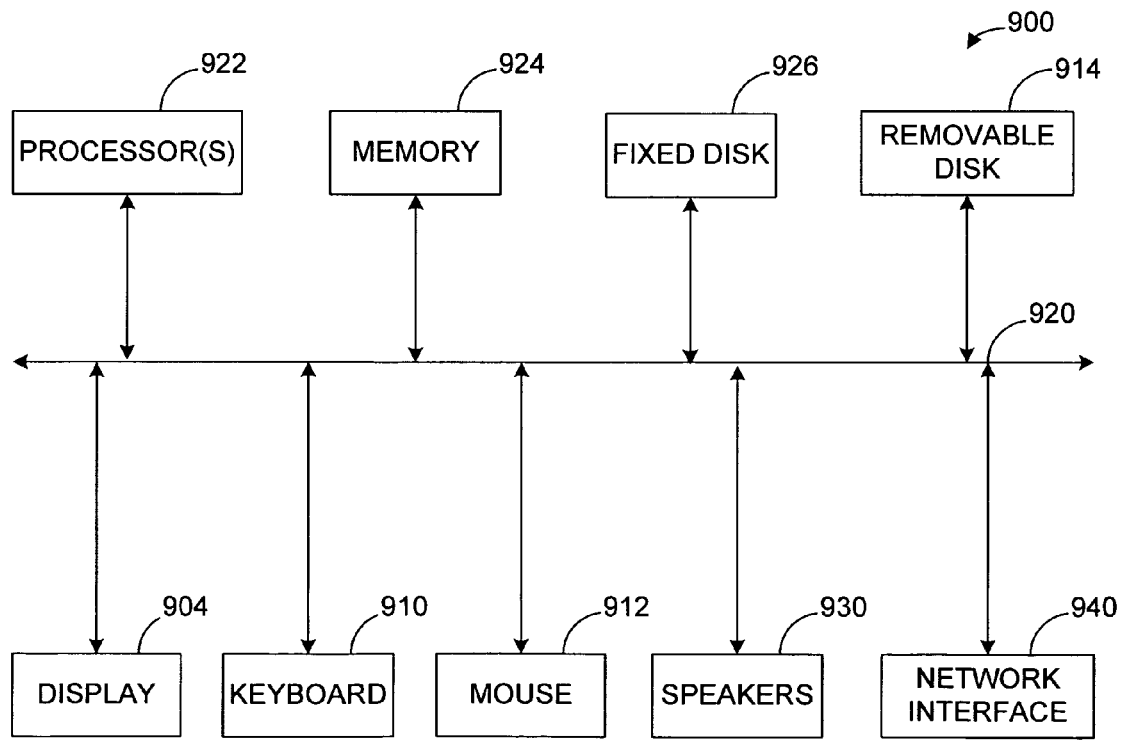

FIGS. 4 and 5 illustrate a computer system 900 suitable for implementing embodiments of the present invention. FIG. 4 shows one possible physical form of the computer system. Of course, the computer system may have many physical forms ranging from an integrated circuit, a printed circuit board and a small handheld device up to a huge super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 5 is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A method for determining an unknown parameter of a semiconductor specimen using a semiconductor inspection system, the method comprising:
    scanning a region of interest with an electron beam to cause X-rays to emanate from the region of interest;
    detecting the X-rays from the region of interest using at least one X-ray detector wherein the detected X-rays are within a certain energy range spectrum and thereby form an experimental X-ray spectrum;
    selecting a reference spectrum from an X-ray spectrum library based upon a set of inspection system parameters, a set of known semiconductor specimen parameters, and an initial estimated value for the unknown parameter;
    generating a simulated spectrum using a spectrum simulation algorithm based upon the set of inspection system parameters, the set of known semiconductor specimen parameters, and the initial estimated value for the unknown parameter, wherein the simulated spectrum is generated when an appropriate reference spectrum is not part of the X-ray spectrum library;
    comparing the experimental X-ray spectrum against either the reference spectrum or the simulated spectrum and determining the degree to which the experimental X-ray spectrum matches either the reference or simulated spectrum;
    when the experimental X-ray spectrum does not match the reference or simulated spectrum to a satisfactory degree, repeating the selecting, generating, and comparing operations wherein a new estimated value for the unknown parameter is used in place of the initial estimated value for the unknown parameter; and
    when the experimental X-ray spectrum does match the reference or simulated spectrum to a satisfactory degree, determining that the estimated value for the unknown parameter used to select the reference spectrum or to generate the simulated spectrum is approximately equal to the actual value of the unknown parameter.

2. A method for determining an unknown parameter of a semiconductor specimen as recited in claim 1 wherein at least some of the inspection system parameters includes electron beam parameters and X-ray detector parameters.

3. A method for determining an unknown parameter of a semiconductor specimen as recited in claim 2 wherein the electron beam parameters includes at least the energy of the electron beam, the incident angle of the electron beam, the raster size and dimensions of the electron beam, and the electron beam current.

4. A method for determining an unknown parameter of a semiconductor specimen as recited in claim 2 wherein the X-ray detector parameters includes at least a detector type, the energy resolution, the reference energy for energy resolution, the solid angle of the detector, and the polar and azimuth angles.

5. A method for determining an unknown parameter of a semiconductor specimen as recited in claim 1 further comprising:
    acquiring an image of the region of interest on the semiconductor specimen; and
    determining, from the image, the values of at least some of the parameters of the set of known semiconductor specimen parameters.

6. A method for determining an unknown parameter of a semiconductor specimen as recited in claim 1 wherein the initial and new estimated value for the unknown parameter is an atomic number, and the unknown parameter describes the material composition of the region of interest.

7. A method for determining an unknown parameter of a semiconductor specimen as recited in claim 1 wherein the simulated spectrum generated with the simulated spectrum algorithm is stored in the X-ray spectrum library.

8. A method as recited in claim 1 wherein the degree to which the experimental X-ray spectrum matches the reference or simulated spectrum is determined by using a simplex mathematical technique during the comparing operation.

9. A method for determining an unknown parameter of a semiconductor specimen as recited in claim 1 further comprising:
    selecting the initial estimate value of the unknown parameter based upon the experimental X-ray spectrum.

10. A method for determining an unknown parameter of a semiconductor specimen using a semiconductor inspection system, the method comprising:
    scanning a region of interest with an electron beam to cause X-rays to emanate from the region of interest;
    detecting the X-rays from the region of interest using at least one X-ray detector wherein the detected X-rays are within a certain energy range spectrum and thereby form an experimental X-ray spectrum;
    generating a simulated spectrum using a spectrum simulation algorithm based upon a set of inspection system parameters, a set of known semiconductor specimen parameters, and an initial estimated value for the unknown parameter;
    comparing the experimental X-ray spectrum against the simulated spectrum and determining the degree to which the experimental X-ray spectrum matches the simulated spectrum;
    when the experimental X-ray spectrum does not match the simulated spectrum to a satisfactory degree, repeating the generating and comparing operations wherein a new estimated value for the unknown parameter is used in place of the initial estimated value for the unknown parameter; and when the experimental X-ray spectrum does match the simulated spectrum to a satisfactory degree, determining that the estimated value for the unknown parameter used to generate the simulated spectrum is approximately equal to the actual value of the unknown parameter.

11. A method for determining an unknown parameter of a semiconductor specimen as recited in claim 10 further comprising:

acquiring an image of the region of interest on the semiconductor specimen; and determining, from the image, the values of at least some of the parameters of the set of known semiconductor specimen parameters.

12. A method for determining an unknown parameter of a semiconductor specimen as recited in claim 10 wherein at least some of the inspection system parameters includes electron beam parameters and X-ray detector parameters.

13. A method for determining an unknown parameter of a semiconductor specimen as recited in claim 10 wherein the initial and new estimated value for the unknown parameter is an atomic number, and the unknown parameter describes the material composition of the region of interest.

14. A method for determining an unknown parameter of a semiconductor specimen as recited in claim 10 wherein the unknown parameter represents either a dimensional aspect of the specimen or a density measurement of the specimen.

15. A method for determining an unknown parameter of a semiconductor specimen as recited in claim 10 wherein each of the simulated spectrums generated with the simulated spectrum algorithm is stored in an X-ray spectrum library.

16. A method as recited in claim 10 wherein the degree to which the experimental X-ray spectrum matches the reference or simulated spectrum is determined by using a simplex mathematical technique during the comparing operation.

17. A method for determining an unknown parameter of a semiconductor specimen as recited in claim 10 further comprising:

selecting the initial estimate value of the unknown parameter based upon the experimental X-ray spectrum.

18. A computer-readable medium comprising computer code for determining an unknown parameter of a semiconductor specimen using a semiconductor inspection system, the computer-readable medium comprising:

scanning a region of interest with an electron beam to cause X-rays to emanate from the region of interest;

detecting the X-rays from the region of interest using at least one X-ray detector wherein the detected X-rays are within a certain energy range spectrum and thereby form an experimental X-ray spectrum;

selecting a reference spectrum from an X-ray spectrum library based upon a set of inspection system parameters, a set of known semiconductor specimen parameters, and an initial estimated value for the unknown parameter;

generating a simulated spectrum using a spectrum simulation algorithm based upon the set of inspection system parameters, the set of known semiconductor specimen parameters, and the initial estimated value for the unknown parameter, wherein the simulated spectrum is generated when an appropriate reference spectrum is not part of the X-ray spectrum library;

comparing the experimental X-ray spectrum against either the reference spectrum or the simulated spectrum and determining the degree to which the experimental X-ray spectrum matches either the reference or simulated spectrum;

when the experimental X-ray spectrum does not match the reference or simulated spectrum to a satisfactory degree, repeating the selecting, generating, and comparing operations wherein a new estimated value for the unknown parameter is used in place of the initial estimated value for the unknown parameter; and when the experimental X-ray spectrum does match the reference or simulated spectrum to a satisfactory degree, determining that the estimated value for the unknown parameter used to select the reference spectrum or to generate the simulated spectrum is approximately equal to the actual value of the unknown parameter.

19. A computer-readable medium as recited in claim 18 wherein the simulated spectrum generated with the simulated spectrum algorithm is stored in the X-ray spectrum library.

* * * * *